(12) United States Patent
Jacques

(10) Patent No.: US 7,648,502 B2
(45) Date of Patent: Jan. 19, 2010

(54) LOW PROFILE SHORT TAPERED TIP CATHETER

(75) Inventor: Steven L. Jacques, Westford, MA (US)

(73) Assignee: Conmed Endoscopic Technologies, Inc., Utica, NY (US)

( * ) Notice: Subject to any disclaimer, the term of this patent is extended or adjusted under 35 U.S.C. 154(b) by 320 days.

(21) Appl. No.: 10/698,496

(22) Filed: Oct. 31, 2003

(65) Prior Publication Data

US 2004/0133148 A1 Jul. 8, 2004

(51) Int. Cl.
*A61B 18/18* (2006.01)
(52) U.S. Cl. .................................. 606/47; 606/167
(58) Field of Classification Search .............. 606/46, 606/47, 170, 200, 39, 127, 128, 167, 129, 606/159; 604/523, 22, 28, 102.02, 105–109, 604/525; 600/373, 567, 585
See application file for complete search history.

(56) References Cited

U.S. PATENT DOCUMENTS

| | | | |
|---|---|---|---|
| 3,634,924 A | 1/1972 | Blake et al. ........... 29/447 |
| 4,474,174 A | 10/1984 | Petruzzi | |
| 4,485,812 A | 12/1984 | Harada et al. | |
| 4,588,398 A * | 5/1986 | Daugherty et al. ........ 604/265 |
| 4,641,654 A | 2/1987 | Samson et al. | |
| 4,724,836 A | 2/1988 | Okada | |
| 5,024,617 A | 6/1991 | Karpiel | |
| 5,271,410 A | 12/1993 | Wolzinger et al. | |
| 5,318,530 A | 6/1994 | Nelson | |
| 5,383,852 A | 1/1995 | Stevens-Wright | |
| 5,397,302 A | 3/1995 | Weaver et al. | |
| 5,437,637 A | 8/1995 | Lieber et al. | |
| 5,464,394 A | 11/1995 | Miller et al. | |
| 5,547,469 A | 8/1996 | Rowland et al. | |
| 5,562,619 A | 10/1996 | Mirarchi et al. | |
| 5,599,299 A | 2/1997 | Weaver et al. | |
| 5,601,582 A | 2/1997 | Shelton et al. | |
| 5,643,199 A | 7/1997 | Rowland et al. | |
| 5,662,620 A | 9/1997 | Lieber et al. | |

(Continued)

FOREIGN PATENT DOCUMENTS

EP 0920882 A2 6/1999

(Continued)

OTHER PUBLICATIONS

Boston Scientific, Autotome RX Cannulating Sphincterotomes, product brochure.*

(Continued)

*Primary Examiner*—Anhtuan T Nguyen
*Assistant Examiner*—Tuan V Nguyen
(74) *Attorney, Agent, or Firm*—Marjama Muldoon Blasiak & Sullivan LLP

(57) ABSTRACT

A low profile, short, tapered distal tip catheter and methods for its manufacture are provided. The catheter tip is configured to have a taper over a relatively short length resulting in a low profile that is useful when navigating the catheter tip into tight passages such as the Papilla of Vater. The configuration of the tip and process for making it can be employed in any medical catheter but are found to be most useful in a multilumen papillotome catheter used in biliary procedures.

16 Claims, 10 Drawing Sheets

U.S. PATENT DOCUMENTS

| | | | |
|---|---|---|---|
| 5,683,362 A | | 11/1997 | Rowland et al. |
| 5,715,817 A | | 2/1998 | Stevens-Wright et al. |
| 5,788,681 A | | 8/1998 | Weaver et al. |
| 5,797,869 A | | 8/1998 | Martin et al. ............... 604/43 |
| 5,810,807 A | | 9/1998 | Ganz et al. |
| 5,843,028 A | | 12/1998 | Weaver et al. |
| 5,868,698 A | | 2/1999 | Rowland et al. |
| 5,919,164 A | | 7/1999 | Andersen ............... 604/102 |
| 5,954,745 A | | 9/1999 | Gertler et al. |
| 5,984,920 A | | 11/1999 | Steinbach |
| 6,017,339 A | * | 1/2000 | Sadamasa ............... 606/46 |
| 6,676,659 B2 | * | 1/2004 | Hutchins et al. ............ 606/47 |
| 6,740,277 B2 | * | 5/2004 | Howell et al. ............ 264/209.3 |
| 7,056,319 B2 | * | 6/2006 | Aliperti et al. ............ 606/41 |
| 2002/0095146 A1 | | 7/2002 | Hutchins et al. ............ 606/39 |
| 2003/0078473 A1 | * | 4/2003 | Richardson ............... 600/115 |
| 2003/0208219 A1 | | 11/2003 | Aznoian et al. |

FOREIGN PATENT DOCUMENTS

| | | |
|---|---|---|
| JP | 4058961 A | 2/1992 |
| JP | 8317969 A | 12/1996 |
| JP | 9206309 A | 8/1997 |
| JP | 11178929 A | 7/1999 |
| JP | 2000296179 A | 10/2000 |
| WO | WO99/17669 | 4/1999 |
| WO | WO 01/56641 A1 | 8/2001 |
| WO | WO-0189412 A2 | 11/2001 |
| WO | WO-0189624 A1 | 11/2001 |

OTHER PUBLICATIONS

510(k) Summary from FDA for Autotome RX Canulaiting Sphincterotome.*
2001, Boston Scientific Microvasive, Products for Endoscopy, Price List and Ordering Information (6 pages).*
"Autotome™ RX Sphincterotomes" product brochure, Boston Scientific Corporation, 2003.
Cotton, Peter B., et al. "Endoscopic Retrograde Cholangio-Pancreatography", Practical Gastrointestinal Endoscopy (Oxford, Blackwell Scientific Publications, Fourth Edition 1996), pp. 105-138.
"Autotome™ Rx" product brochure, Boston Scientific/Microvasive 2002.
"2002 Price List and Ordering Information, Products for Endoscopy", Boston Scientific/Microvasive (pp. 4, 7-8, 11-13).
"Howell DASH Direct Access System", "Babytome Precurved Double Lumen Sphincterotomes" and "Minitome" product brochure, Wilson Cook 2002.
International Search Report for corresponding PCT Application No. PCT/US03/34973, dated Jun. 25, 2007 (3 pgs.).
Written Opinion for corresponding PCT Application No. PCT/US03/34973, dated Jun. 25, 2007 (4 pgs.).

* cited by examiner

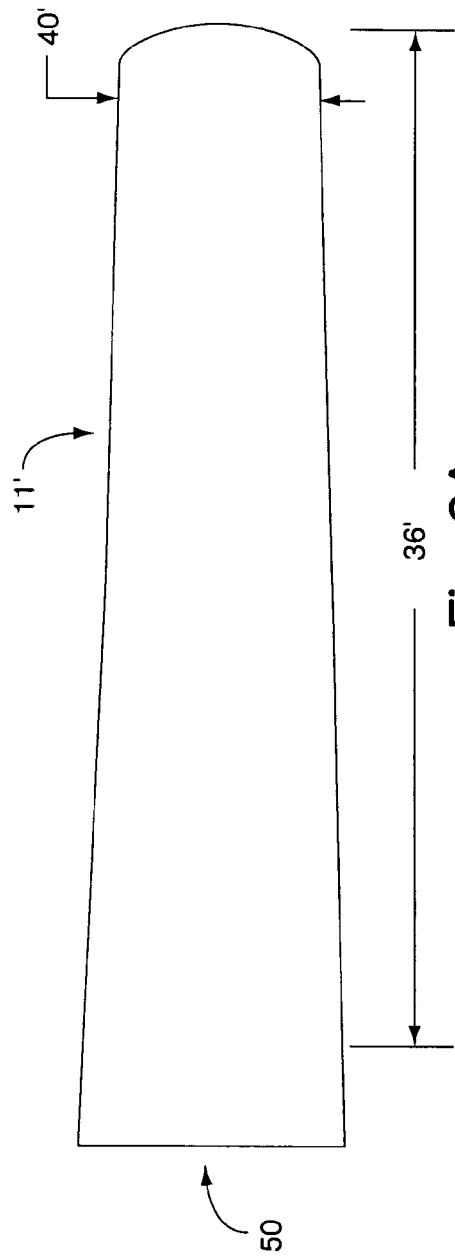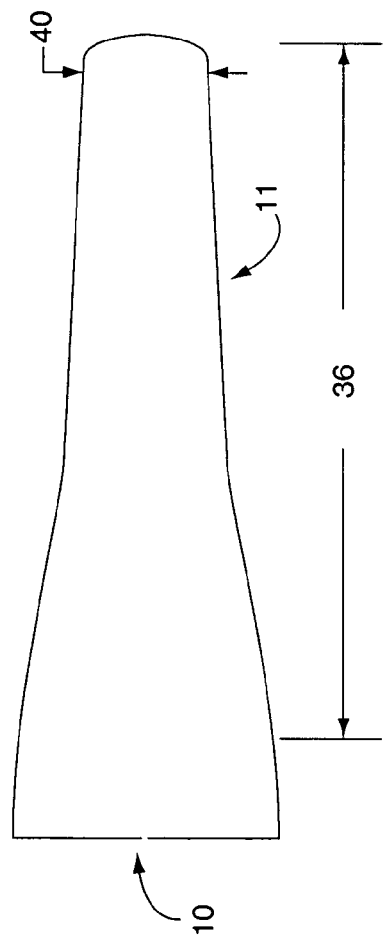
Fig. 3A (PRIOR ART)
Fig. 3B

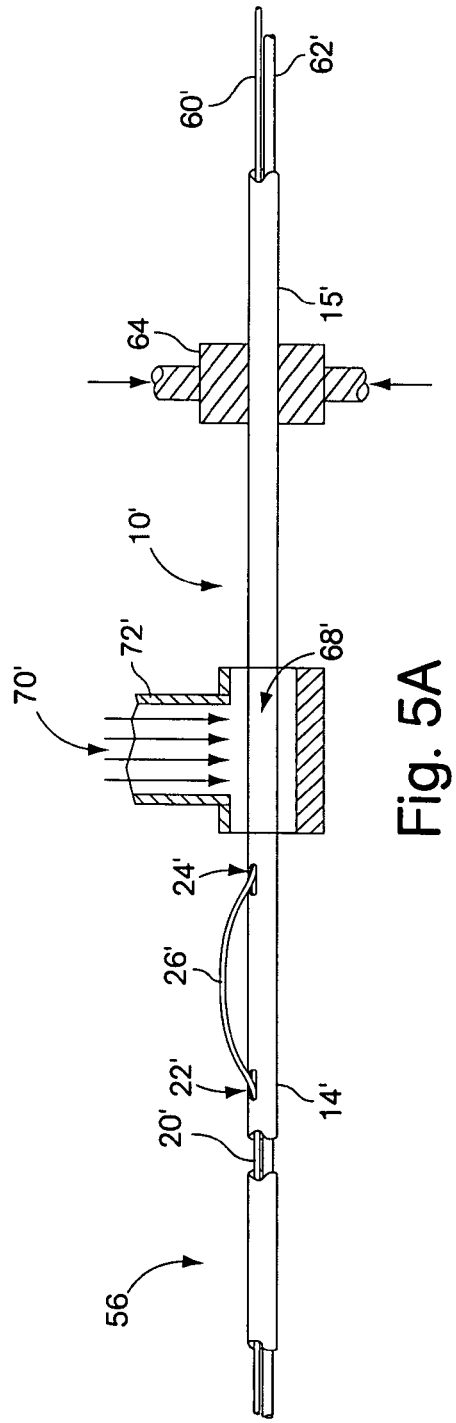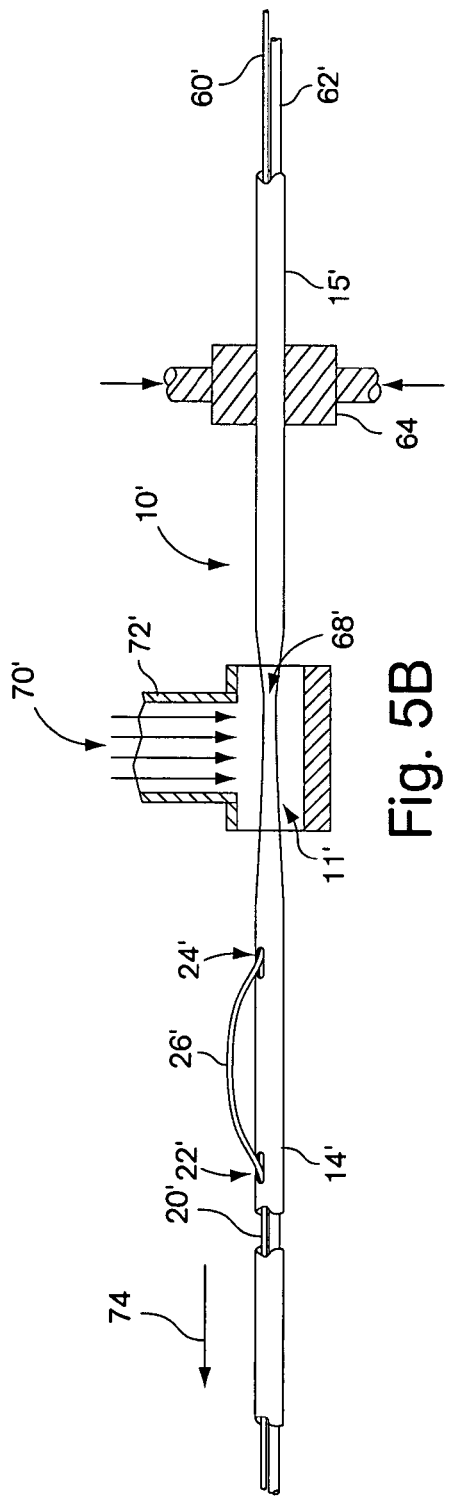
Fig. 5A (PRIOR ART)
Fig. 5B (PRIOR ART)

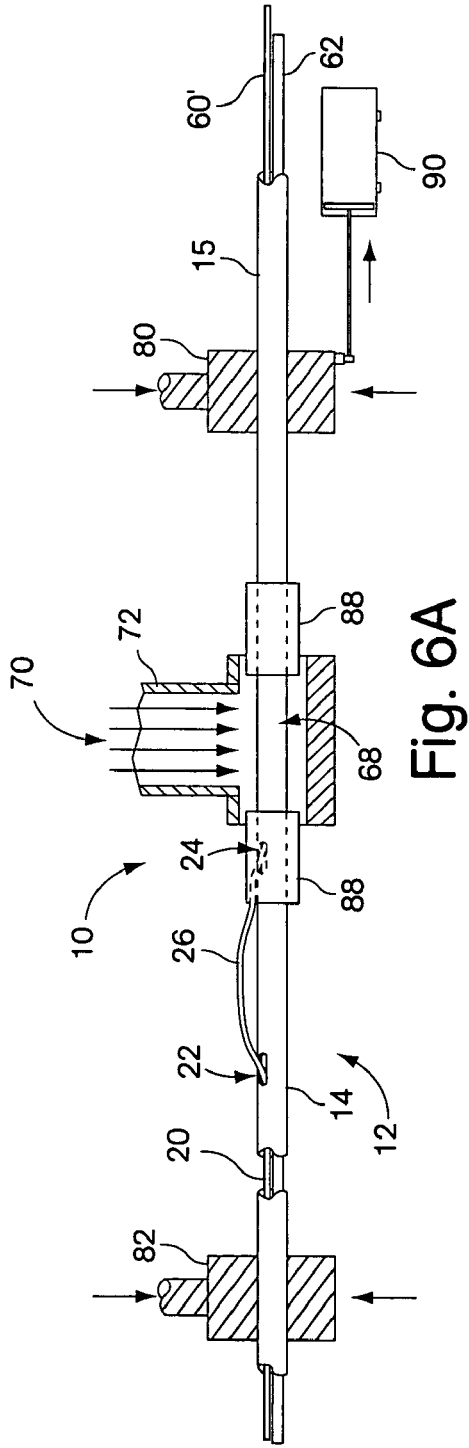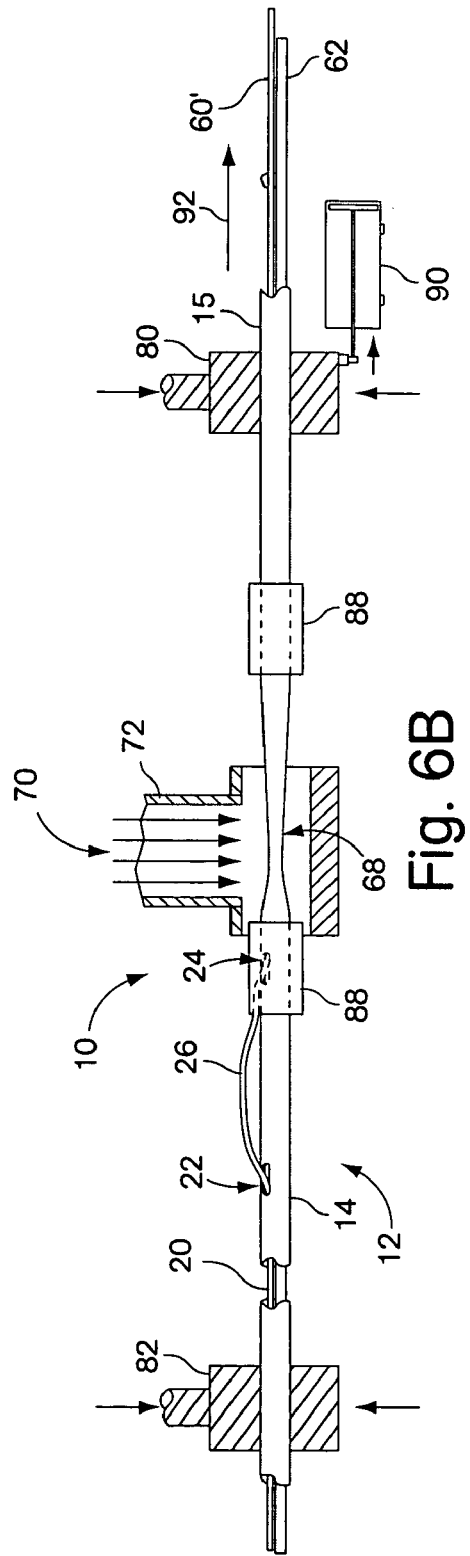

ical catheters. In particular, catheters having distal tip configurations that are tapered to provide a low profile and methods for manufacturing catheters with such configurations.

LOW PROFILE SHORT TAPERED TIP CATHETER

FIELD OF THE INVENTION

The present invention relates to medical catheters. In particular, catheters having distal tip configurations that are tapered to provide a low profile and methods for manufacturing catheters with such configurations.

BACKGROUND OF THE INVENTION

Catheters are elongate flexible instruments navigated through natural body lumens of a patient to serve as a conduit for performing a medical procedure at a remote location in the human body. Because the catheters are small and can be navigated through passageways that already exist naturally in the body, the invasiveness of the procedure is minimized. Minimizing trauma associated with the procedure reduces risk to the patient and costs for the medical care provider. In catheter design, there are two prominent design objectives that require conflicting design configurations in order to be achieved. First, is the necessity to make the catheter as small profile as possible to minimize trauma to the patient and to facilitate navigation through narrow passages in the anatomy. The second design consideration is to make the interior passages of the catheter large enough to easily accept other instruments or to provide passage for fluid delivery or aspiration. Of course, reducing the profile of the catheter impinges on the amount of space available to accept instruments and fluid passageways through the catheter that are needed to carry out the medical procedure. The challenge of making a catheter of small profile is especially difficult in designs that employ multiple lumens through the catheter to accept one or more instruments or fluid passageways simultaneously.

In all catheter designs, perhaps the most crucial area for maintaining a reduced profile is at the distal tip of the catheter. The distal tip is the leading area of the catheter as it is navigated into a body lumen and to a treatment site. A small profile at the distal tip of the catheter facilitates penetration through small openings and expands them gradually as the wider more proximal areas of the catheter shaft proceed through.

Biliary procedures in which the Papilla of Vater must be cannulated in order to access the common bile duct can be especially challenging. The papilla is a natural orifice at the end of the common bile duct that is surrounded by the sphincter muscle, which can keep the opening tightly closed. In a biliary procedure, an endoscope is navigated to a location adjacent the papilla and a biliary catheter is inserted through the endoscope and extended through the distal port of the scope. The catheter is advanced to enter the papilla and common bile duct to carry out a biliary procedure such as stone removal or stenting. Failed attempts to cannulate the papilla can serve to irritate it, making it even more difficult to penetrate. Special biliary catheters called papillatomes have been developed that employ an RF energized cutting wire to make a small cut in the papilla during cannulation to increase the diameter of the passage and facilitate penetration. The small cut in the papilla also may serve as effective treatment to allow stones trapped in a bile duct to pass freely through the papilla. Despite the presence of a cutting wire on the papillatome catheter, an effective low profile tip is still desirable to help facilitate entry and positioning of the papillatome in the papilla. The smaller the diameter of the tip of a papillatome, the easier it will be to insert into the small or closed opening of the papilla.

In a biliary catheter such as a papillatome it is also desirable to have a relatively short tip length between the distal end of the tip and the beginning of the exposed cutting wire. The distance between the entry to the common bile duct at the papilla and the first junction in the common bile duct (the segment known as the intramural segment) is 2-8 mm. The Y-shaped junction splits the common bile duct into the pancreatic duct and the bile duct. After cannulation of the papilla the option to proceed into the either duct must remain available to the physician. However, if the tip length of the catheter is relatively long, such as 8 mm or greater, the distal tip may already be positioned beyond the junction after cannulation with the cutting wire at the papilla. With the tip in one duct or the other, selection of the other duct is difficult. A short tip catheter with a tip length distal of about 5 mm or less would be more likely not to extend beyond the junction of the common bile duct after cannulation, thus facilitating navigation into the desired duct for treatment. Also a shorter tip length provides the user with more control over the orientation of the papillatome tip during use. A short tip length also reduces the length of catheter that must be inserted before the exposed cutting wire reaches the papilla and cutting can begin.

As stated above, among the design considerations for a catheter, and in particular a papillatome catheter is providing sufficient space through the interior of the catheter so that other instruments and fluid channels can be provided through the device. Providing multiple lumens in the catheter shaft is one way to enhance the utility of the catheter as a conduit for other devices and treatments. In particular, two or three lumen papillatomes are desirable so that individual lumens can be provided for the cutting wire, a guidewire and a separate lumen for contrast media injection. Not only is it desirable to provide multiple lumens in a papillatome catheter, but also there is a need to make the lumens as large as possible. It is desirable to provide a separate contrast injection lumen, in which a larger diameter helps to insure that the sticky, viscous contrast media can be injected freely at pressures that are easy to modulate. A large guidewire lumen is desirable such that a relatively stiff guidewire providing good pushability performance, such as a 0.035 inch stainless steel guidewire, can be used to track the papillatome catheter and any subsequent catheters that may be navigated into the common bile duct during the procedure.

In current catheter design, attempts to address all the above design considerations in one catheter leads to compromises of each design objective. Provision of multiple large lumens compromises the ability to provide a low profile distal tip. Though tapering the tip to a reduced profile is one way to address that compromise, tapering the tip to a very low profile over a short distance to provide a short tip length is difficult because wall thickness necessarily becomes reduced to the point where lumens and components within them can be exposed to other lumens or to the exterior of the shaft.

When a catheter of sufficiently low profile to access a tight opening such as the papilla is not available in a size to sufficiently large to accommodate the desired instruments such as a 0.035 inch guidewire, a specialized low profile catheter may be used to start the procedure. However such specialized small catheters are not large enough to receive the larger diameter 0.035 inch guidewire, suitably stiff for carrying out all the steps of a biliary procedure such as permitting exchange of different catheters over it. Instead a specialized low profile catheter sacrifices lumen size to provide the low profile. The reduced lumen size may hinder or prevent certain procedures required to be conducted through the catheter. In a biliary procedure, the largest diameter guidewire usable with such a catheter may be only 0.025 inch. That small diameter guidewire is not sufficiently stiff to provide acceptable pushability or to perform catheter exchanges. Therefore if the low profile catheter is first used to cannulate the papilla, the catheter must then be exchanged, for a larger catheter and then the guidewire exchanged for a larger (0.035 inch) guidewire before the procedure can continue. This additional exchanging activity increases procedure time and risk to the patient.

It would be desirable to provide a catheter that combined the attributes of a low profile tapered distal tip, of a short length and having sufficiently large lumen sizes to accommodate the instruments required for all aspects of the procedure. In particular, it would be desirable to provide a papillatome catheter configured to accommodate a 0.035 inch guidewire yet having a low profile distal tip and a short tip length so that exchanges to use a catheter and guidewire useful solely for cannulating the papilla would not be required. It is an object of the present invention to provide a catheter having a distal tip with a low profile, short length and suitably large lumen sizes and arrangements and methods for manufacturing it.

SUMMARY OF THE INVENTION

The present invention provides a catheter having a low profile short tapered distal tip while maintaining the lumen capacity of a comparable catheter without a low profile tapered short tip configuration. The inventive catheter and process for its manufacture may be employed on catheters for any purpose but are especially useful as applied to papillatome catheters used in biliary procedures. A papillatome catheter benefits especially from the present invention because it requires that lumen capacity through the distal tip be maintained in order to accommodate a guidewire, cutting wire and preferably a dedicated flow channel for contrast media yet the distal tip must be a low profile and relatively short in order to facilitate cannulation of the papilla. A two lumen or three lumen papillatome catheter of the present invention may have a distal tip section (distal to the distal exposed end of the cutting wire) that is approximately 5 millimeters in length and presenting a profile that is approximately 4.5 French (0.059 inch) while still accommodating through its guidewire lumen a 0.035 inch diameter guidewire.

The low profile short tapered distal tip is formed by new process that forms a taper in the tip by applying heat only in a specific limited area that is to be formed. Before the polymer shaft is heated and stretched to create the taper, thermally insulative segments such as pieces of polyolefin heat shrink tubing are placed proximally and distally to the forming area that will become tapered on the distal tip. The insulative segments serve to keep surrounding areas of the shaft thermally stable while only the forming area is heated to a point at which it may become plastically deformed. After the insulative segments are placed and secured by heat shrinking to the shaft, the shaft is grasped proximally and distally of the forming area and stretched by pulling the distal clamp in a distal direction away from the stationary proximal clamp in order to stretch and neck the forming area, creating a taper. The insulative segments are preferably configured to provide radially compressive support to the shaft segments to prevent stretching of the shaft material beneath them. After the heating and stretching process, the shaft may be cooled and insulative segments removed to provide a finished low profile tapered catheter tip.

The invention also permits the low profile tapered tip to be applied over a shorter tip length to further enhance the penetration and performance qualities of the resulting catheter tip. Specifically, the low profile tapered tip described above, may be applied to a papillatome catheter over a tip length of approximately 5 millimeters. The papillatome made according to the present invention incorporates a shorter tip by utilizing shortened anchoring and radiopaque components in the distal tip assembly. The insulative segments keep help to define the forming area over a defined, limited length so that the taper forms over only that limited length during the stretching process. The resulting catheter tip is about 3 millimeters shorter than previously known catheter tips having a 4.5 French profile and 0.035 inch guidewire compatibility.

The dimensional improvement results in a significant performance improvement when used to cannulate the papilla during a biliary procedure. The low profile tip can enter the papilla more easily and the short tip length facilitates navigation in the common bile duct immediately following penetration so that lumen selection in the intraluminal segment remains an option. It is expected that the short tip length of approximately 5 mm will enable the physician to navigate the tip into either the pancreatic duct or the bile duct from the intraluminal segment of the common bile duct after cannulation of the papilla. Additionally, the short tip length to the distal end of the cutting wire expedites the moment at which cutting of the papilla can begin during cannulation.

The process also permits a lumen size that still accommodates the larger instruments used with previously known catheters such as the 0.035 inch guidewire. The confined application of heat in combination with placement of forming mandrels to locate embedded components results in lumens defined through the tip that have sufficiently robust wall thickness to ensure adequate performance during use.

It is an object of the present invention to provide a catheter having a low profile short tapered tip that maintains the lumen capacity of a conventional tapered tip catheter.

It is an object of the present invention to provide a process for producing a low profile distal tapered tip on a catheter that is economical and simple to manufacture.

It is another object of the present invention to provide a low profile short tapered tip triple lumen papillatome having three lumens including a guidewire lumen configured to accept a 0.035 inch guidewire in which the distal tip has a profile of approximately 4.5 French and a length of approximately 5 millimeters.

It is another object of the invention to facilitate new methods of catheterizing natural body lumens by using a low profile short tapered tip catheter.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 3A is a depiction from a photograph of a prior art distal tip of approximately 8 mm in length. FIG. 3B is a depiction from a photograph of a distal tip according to the present invention, tapered over a 5 mm length shown for comparison to the prior art tip of FIG. 3A.

FIGS. 5A and 5B are diagrammatic illustrations of a papillatome catheter undergoing a prior art necking process to produce a tapered distal tip;

FIGS. 6A and 6B are diagrammatic illustrations of a papillatome catheter undergoing a necking process to form a tapered distal tip according to the present invention;

DESCRIPTION OF THE ILLUSTRATIVE EMBODIMENTS

Figure 1:
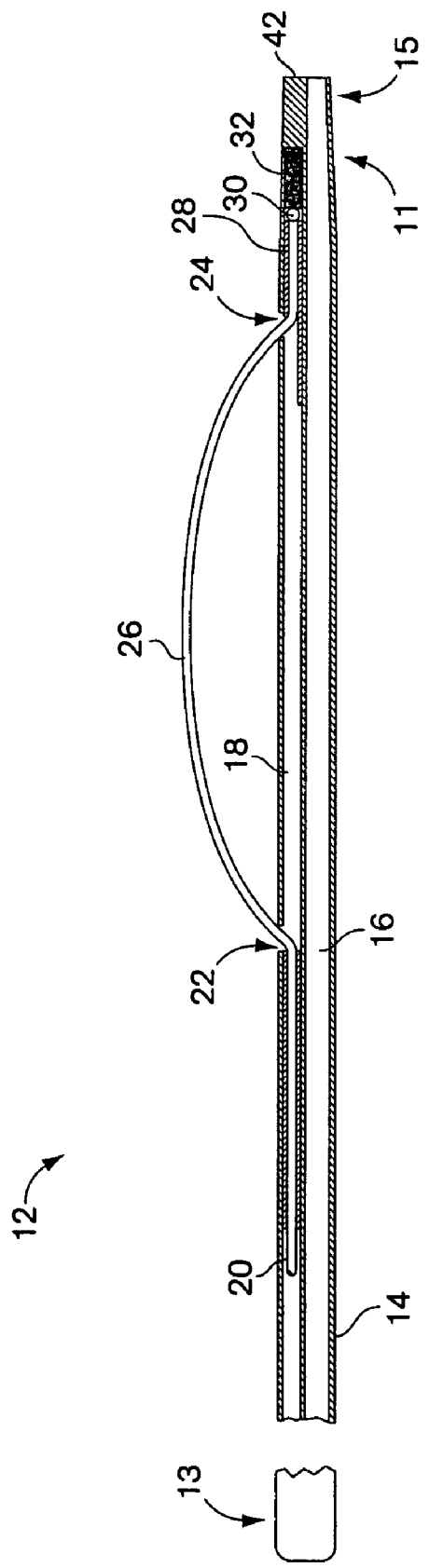
FIG. 1 is a side sectional view of a papillatome catheter embodying the present invention.
Figure 9A:
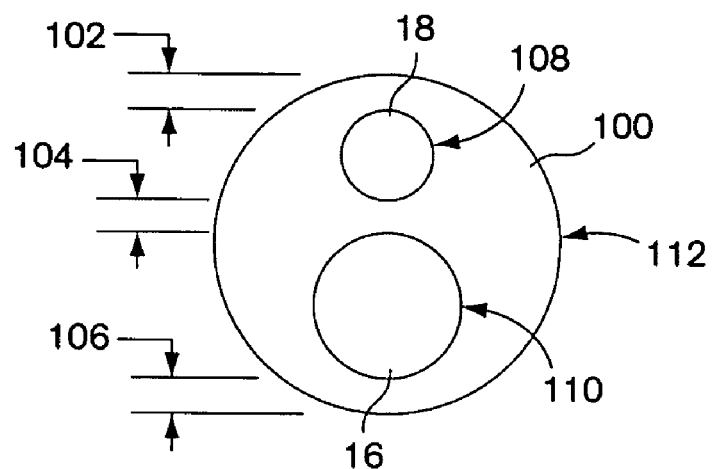
FIG. 9A is a cross sectional illustration of a two lumen shaft suitable for forming the low profile short tapered tip of the present invention.
Figure 9B:
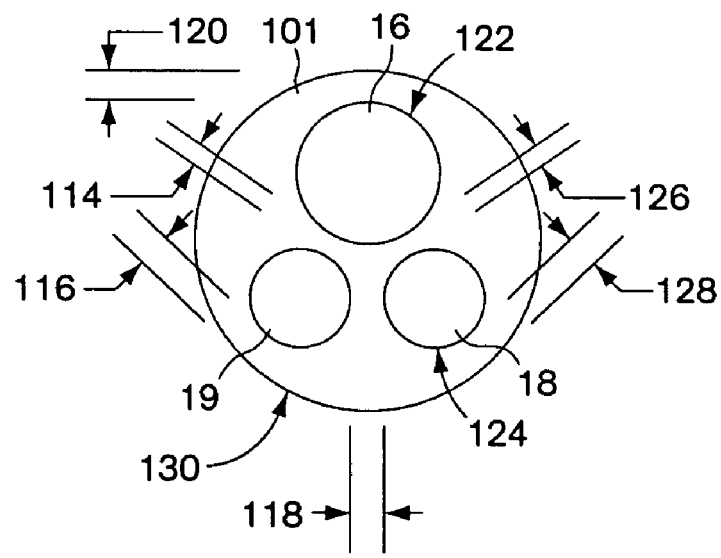
FIG. 9B is a cross sectional illustration of a three lumen shaft suitable for forming the low profile short tapered tip of the present invention.

FIG. 1 shows the distal portion of a papillatome catheter 12 employing the low profile short tapered tip 10 of the present invention. The papillatome catheter comprises a shaft 14 having a proximal end 13 and a distal end 15. The tip 10 at the distal end 15 of the shaft has a tapered portion 11 over which the tip diameter is gradually reduced. Through the shaft may extend a plurality of lumens 16 and 18. In the example of a papillatome shown in FIG. 1, a large lumen 16 is sized to receive a guidewire of a diameter of approximately 0.035 inch. Another lumen 18 may be configured to receive a cutting wire 20 that is selectively energizable with RF energy to perform cutting of the papilla during cannulation in a biliary procedure. Additionally, a third lumen may be provided for the dedicated purpose of contrast media injection. The third lumen would not be seen in the sectional side views of FIGS. 1 and 2 as it would be positioned behind the cutting wire lumen 18. However, cross-sectional views of two lumen 100 and three lumen 101 shafts are shown in FIGS. 9A and 9B respectively. The arrangement of guidewire lumen 16, cutting wire lumen 18 and a contrast media lumen 19 (FIG. 9B only) are shown. The shaft material is a polymer, preferably Teflon (PTFE).

The cutting wire has a working portion 26 that extends for a limited distance along the exterior of the shaft 14 so that it may come into contact with tissue of the papilla during use. The cutting wire exits the lumen 18 at proximal skive hole 22 and re-enters the lumen 18 at distal skive hole 24. The cutting wire is anchored in the lumen 18 adjacent the distal end 15 of the shaft by means such as a split collet anchor 28 welded to or capturing a bulbous distal tip 30 of the cutting wire. One way to assemble the cutting wire with the catheter is to load into the lumen 18 at the proximal end 13 of the catheter and advance it until the distal end of the wire protrudes through the proximal skive hole 22. Next the split collet anchor 28 may be welded to the distal end of the cutting wire with the fingers of the split collet splayed and pointing in a generally proximal direction. The distal end of the cutting wire and attached anchor may then be loaded into the distal skive hole and advanced distally slightly into the portion of the lumen 18 that is distal to the distal skive hole 22. With the direction of the splayed fingers of the anchor facing proximally, the anchor can be inserted into the lumen in a distal direction, but tension in the proximal direction causes the fingers of the anchor to grip into the lumen side wall anchor to resist movement. Additionally, adhesive may then be placed into the lumen 18 to further secure the anchor in place. To aid in the formation of shorter tip, the length of the anchor 28 has been reduced in length to about 6 mm from about 8 mm, which may normally be used for an anchor to secure a cutting wire.

Additionally, a radiopaque marker 32 may be added to the distal end 15 of the catheter. In the catheter shown in FIGS. 1 and 2 the radiopaque marker comprises a tantalum slug inserted into the lumen 18 from the distal terminus 42 and advanced to be distal to the cutting wire anchor 28 and then sealed in place by the tip forming operation that will be described in detail below. The radiopaque slug may also be shortened in length over the length that may normally be used to in a papillatome catheter in order to create a shorter tip length. For example if the length of a slug normally used measures about 0.079 inch, reducing the length to 0.060 inch permits formation of a shorter tip while still providing an adequate radiopaque marker to identify the distal end of the catheter during use. It is emphasized, that the invention may be practiced with other types of catheters but has been found to provide a particularly useful application with a papillatome catheter. For this reason, the invention is explained in the context of application to a papillatome catheter.

Figure 2:
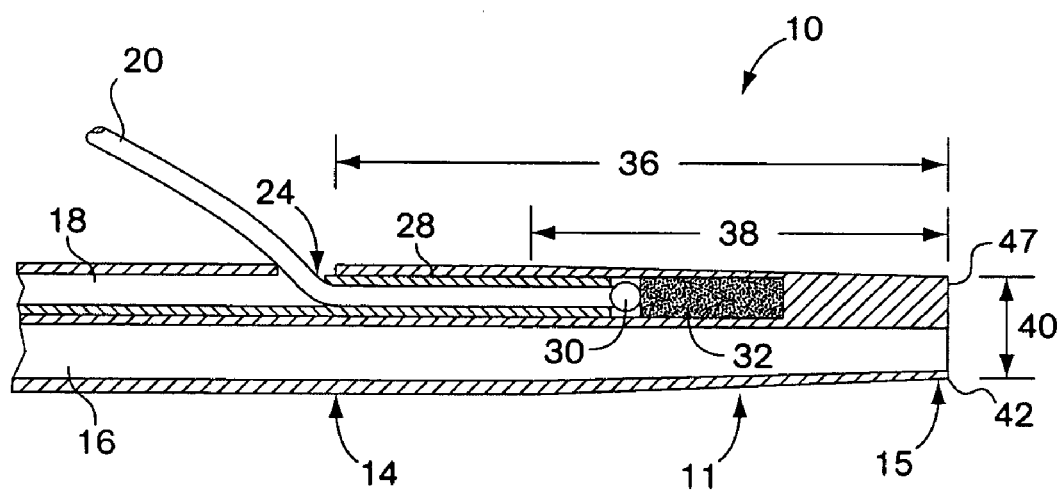
FIG. 2 is a detail of the distal tip of the catheter shown in FIG. 1.

FIG. 2 shows a detailed sectional view of the tapered distal tip 10 of the present invention. In the figure are identified several important dimensions of the low profile short tapered tip of the present invention. The tip length 36 is referenced as dimension A. The taper length 38 is referenced as dimension C, and the distal tip diameter 40 is referenced as dimension B. The tip length 36 is measured from the distal end of the distal skive hole 24 to the distal terminus 42 of the shaft 14. The taper length 38 is measured from the beginning of the taper along the distal tip 10 to the distal terminus 42 of the shaft. The tip diameter 40 is measured at or adjacent to the distal terminus 42 of the shaft. Diameter measurement is more accurate taken slightly proximal to the terminus due to drastic curvature at the very end of the tip that results from the radiusing of the tip in processing to promote smoothness. In a preferred embodiment, a low profile short tapered tip of the present invention will have a tip length 36 (dimension A) on the order of approximately 5 mm and preferably within the range of 4.5 to 6 mm. The tip will have a taper length 38 (dimension C) on the order of approximately 3 mm and preferably within the range of 1.5 mm to 4.5 mm. The tip will have a diameter 40 (dimension B) of 0.059 inch (a circumference of approximately 4.5 French) and preferably within the range of 0.055 inch to 0.063 inch.

The significance of the reduced dimensions of the inventive tip are best appreciated by viewing the depictions shown in FIGS. 3A and 3B, taken from photos, comparing a prior art distal tip with a distal tip of the present invention. In FIG. 3A a prior art catheter distal tip 50 is aligned next to a low profile short tapered tip 10 of the present invention. The tip 10 of the present invention, shown in FIG. 3B, has a tip length 36 (dimension A) of approximately 5 mm. The tip length 36' (dimension A' of the prior art tip 50) measures approximately 8 mm. The diameter 40 (dimension B) of the inventive tip 10 is approximately 0.059 inch (circumference of 45 French), while the diameter 40' (dimension B' of the prior art tip 50) is 0.064 inch (circumference of 5 French).

Figure 4A:
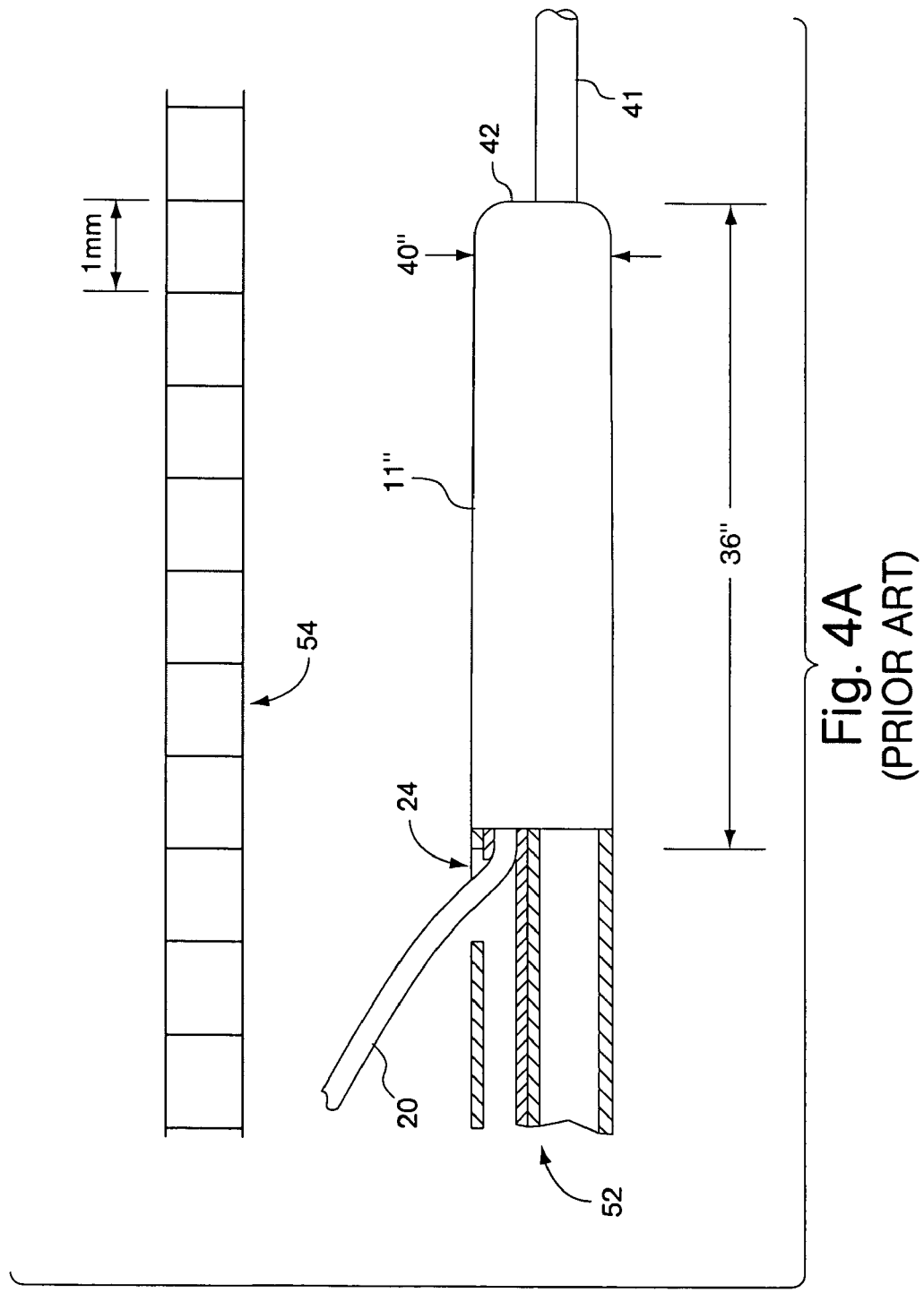
FIG. 4A is a depiction from a photograph of a prior art papillatome distal tip.
Figure 4B:
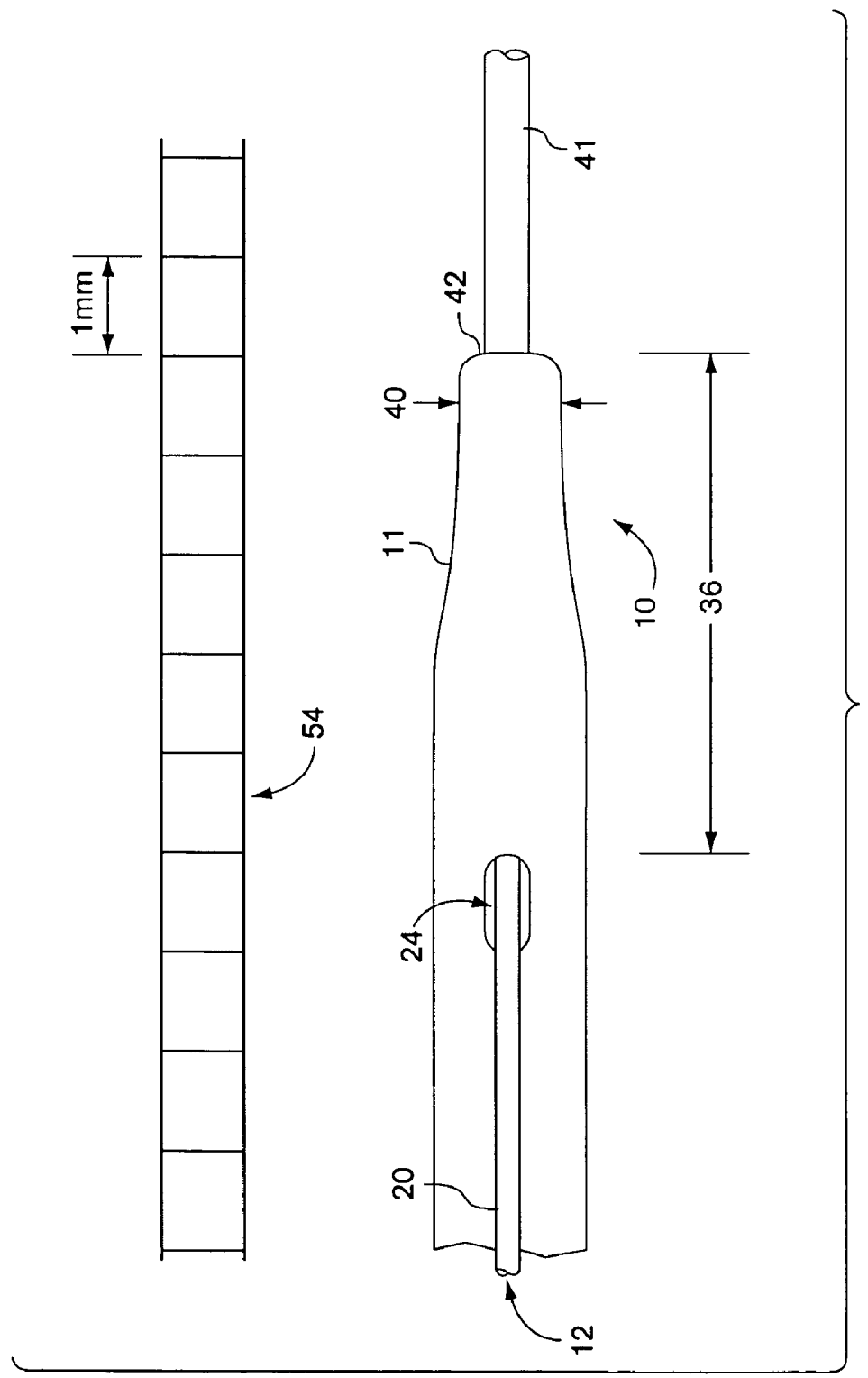
FIG. 4B is a depiction from a photograph of a papillatome distal tip according to the present invention shown for comparison to the prior art tip of FIG. 4A.

In FIG. 4B a papillatome catheter 12 having the low profile short tapered tip 10 of the present invention is shown in comparison to a prior art papillatome 52 (FIG. 4A), both shown lying adjacent a measurement grid 54 showing marked length increments of 1 mm. The tip length 36 (dimension A) of the inventive papillatome tip is approximately 5 mm, while the tip length 36" (dimension A") of the prior art papillatome 52 is approximately 7 mm. The diameter 40 (dimension B) of the present papillatome tip 10 is approximately 0.059 inch (approximately 4.5 French in circumference), while the diameter 40" (dimension B" of the prior art papillatome 52) is approximately 0.064 inch (approximately 5 French in circumference). These figures illustrate the dimensional advantage of the distal tip of the present invention over the prior art catheter distal tips. A 0.035 inch guidewire 41 is represented passing through the guidewire lumen 16 of each tip shown in FIGS. 4A and 4B.

The dimensional improvements provided by the present invention are made possible at least in part by improvements made in the taper forming process applied to the distal tip of the catheter shaft. FIGS. 5A and 5B illustrate the steps of a prior art taper formation process. It is noted that the prior art taper forming process as well as the inventive taper forming process are conducted prior to a final trim cut of the distal tip of the shaft. Therefore, in FIGS. 5A-5B and FIGS. 6A-6B that follow, the distal tip appears to be much longer than that of the final completed assembly, extending some distance distal to the distal skive holes 24 and 24'. During this part of the forming process, the elongated distal tip is useful to provide an area for grasping so that the heated forming area may be stretched by pulling. After the tapering process the tip is trimmed just distal to the end of the taper portion 11, resulting in the tip length shown in the previous figures.

In both the prior art and current tapering processes the polymer shaft 14 area to be tapered may be the product of a previous necking operation to reduce its diameter. For example, a Teflon papillatome shaft may initially be a diameter of 0.096 inch and then be drawn through a hot die with appropriate mandrels inserted through its lumens, to reduce the diameter to 0.079 inch. This first reduced diameter may be formed along a distal portion of the shaft, then, with the next tapering operation, to be described below, the tip diameter is further reduced in profile. The resulting catheter then has two steps of reduced diameter and the original large diameter over its length. The decreased diameter at the distal regions of the catheter permits navigation through small passages in the body, while at the proximal end, which remains outside the patient, a larger diameter is acceptable.

In FIG. 5A, a prior art papillatome 56 is undergoing the initial steps of a prior art tapering process. Components that are the same as those in the present catheter and process are identified in the prior art explanation by the same reference numeral accompanied by a prime symbol. Forming mandrels 60' and 62' are inserted into the lumens of the catheter shaft 14'. The distal end of the shaft 15' is grasped by a mechanical clamp 64. Heat is applied to a forming area 68' by a hot air stream 70' injected through a hot air nozzle fixture 72'. The positioning of the catheter in the hot air stream 70' is such that the forming area 68' will be located proximal to the point of grasping by the clamp 64 and just distal to the distal skive hole 24'. After sufficient heating, the shaft 14' of the prior art papillatome 56 is grasped by hand at a point proximal to the proximal skive hole 22'. The shaft is manually pulled in a proximal direction 74 while the clamp 64 holds distal end 15' stationary.

As shown in FIG. 5B, as the shaft is pulled proximally away from the stationary clamp 64, the forming area 68', having been heated sufficiently to permit plastic deformation, begins to stretch and narrow. When the stretching is complete, the transition from the narrow region to the more proximal areas of the shaft adjacent the distal skive hole 24 that were not heated completely forms the tapered area 11'. The tapered area constitutes the transition from the shaft diameter prior to stretching to the narrowed forming region 68'. After the stretching is complete, the heating may be discontinued cooling of the area permitted and the catheter released from the clamp. Lastly, the distal tip may be trimmed to length and the distal terminus radiused to provide a smooth edge on the final product.

The inventive taper forming process is illustrated in FIGS. 6A and 6B and is discussed below. The shaft 14 used in the below described steps has been previously reduced in diameter by a hot die necking as described above, though the inventive process is expected to perform equally effectively with similar sized shaft material that has not undergone a previous hot die necking operation. In an example of a preliminary necking process, necking a 0.096 inch triple lumen Teflon shaft to 0.079 inch, forming mandrels are first inserted into the lumens; 0.037 inch mandrel is placed through the guidewire lumen, a 0.023 inch forming mandrel is placed through the cutting wire lumen, and a 0.020 inch mandrel is placed through the contrast injection lumen. In a necking machine, a die having a 0.081 inch nominal ID is heated to approximately 475 degrees F. and pressure is set to 95 psi. The shaft is pushed through the die initially, then clamped on the through side of the die and pulled by a mechanized drive system for a length as desired before it is released. The resulting OD of the shaft segment necked by this process is approximately 0.079 inch. It is this necked segment of the shaft that is used in the inventive taper forming process described below.

Figure 7:
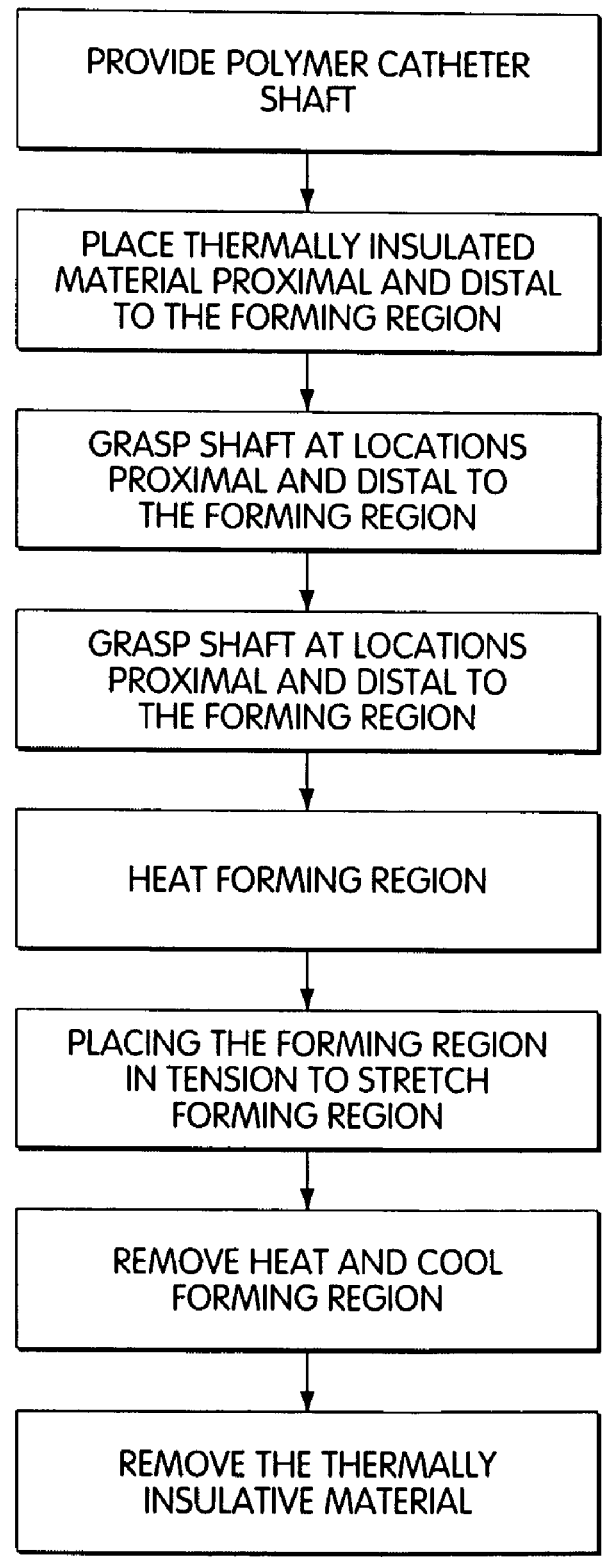
FIG. 7 is a flow chart diagram illustrating the general steps of forming the low profile short tapered tip of the present invention.
Figure 8:
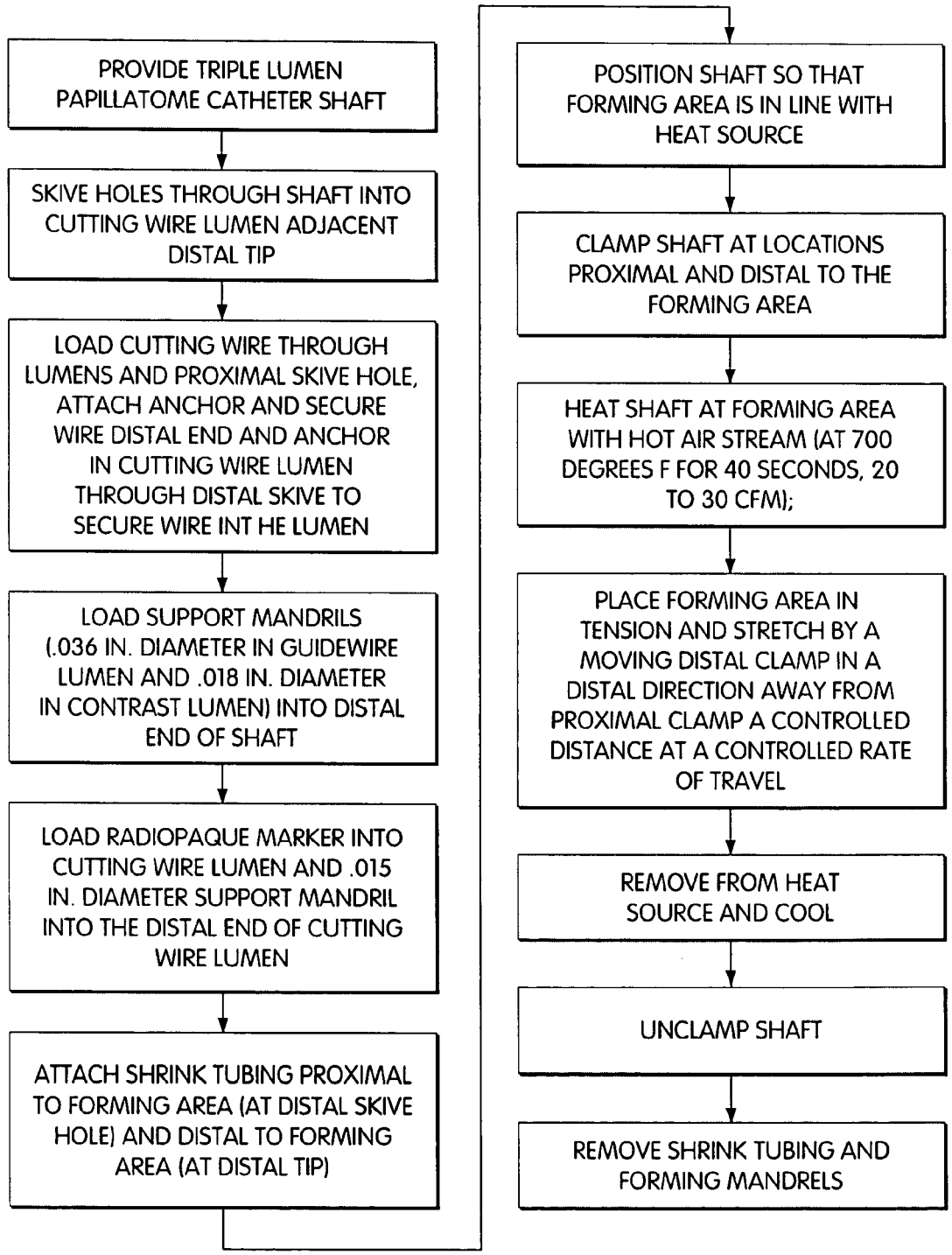
FIG. 8 is a flow chart illustrating the detailed steps for forming a low profile tapered short distal tip for a papillatome catheter according to the present invention.

FIG. 7 provides a flow chart representation of the basic steps of the inventive process applicable to any catheter. FIG. 8 presents a flow chart representation of process steps specific to a 3-lumen papillatome using specific materials and parameters. Reference to FIGS. 7 and 8 may be made in connection with the following process description below illustrated in FIGS. 6A and 6B.

In FIG. 6A, a papillatome 12 is prepared for the inventive taper forming process by insertion of forming mandrels 60 and 62 into the lumens of the catheter. In a three lumen catheter, a 0.036 inch diameter mandrel is inserted into a guidewire lumen 16 and a 0.018 inch mandrel may be inserted into the contrast injection lumen 19, from the distal end 15 of the shaft 14. Though the anchor 28 and bulbous distal tip 30 of the cutting wire 20 are already inserted into the cutting wire lumen prior to the taper forming process, if a radiopaque marker 32 is to be installed, it is then inserted into the cutting wire lumen 18 at the distal end 15 of the shaft and advanced into abutted engagement with the bulbous tip 30 of the cutting wire (positioning shown more clearly in FIG. 1). To help ensure that sufficient catheter material is left in place to provide structural integrity to the short tip after heat forming, the radiopaque marker that is used may be made shorter in length than a marker used in prior art devices so that less is occupied by non-catheter material. Prior to the taper forming process, a 0.015 inch forming mandrel is then inserted from the distal end 15 of the shaft into the cutting wire lumen to abut and hold in place the radiopaque marker 32 during forming of the taper.

Next, in a step not performed in the known prior art forming method, thermally insulative segments 88 are positioned over the shaft 14 and positioned to thermally protect areas immediately proximal and distal to the forming area 68. Though a variety of thermally insulative materials may be employed to provide adequate insulation to the shaft 14 from the heat that will be applied from the hot air stream 70, a convenient material has proven to be polyolefin shrink tubing such as Cole-Flex type ST-221 available from Nova Industries, 344 Boston Post Rd., Marlboro Mass. In its initial diameter, the shrink tubing is sufficiently large to be slid over the shaft 14 then secured in the desired location by application of a light hot air flow, which causes the tubing to shrink about the shaft 14, holding the shrink tubes in the desired position. The segments may be on the order of approximately ¼ inch long. As shown in FIG. 6A, the thermally insulative segments 88 are positioned immediately proximal and distal to the location of the heated airflow 70 on the forming region 68. In the example of a papillatome catheter 12, the proximally insulative segment 88 is positioned directly over the distal skive hole 24. The distal thermally insulative segment is positioned just distal to the area to be heated 68, approximately 8 mm from the proximal insulative segment, as is shown in FIG. 6A.

After positioning of the thermally insulative segments 88, the shaft is grasped by mechanical clamps 80 and 82, both distal and proximal to the forming region 68. As shown in FIG. 6A, the distal clamp 80 may be positioned anywhere on the distal tip 15 between the distal insulative segment 88 and the distal terminus of the catheter shaft. The proximal mechanical clamp 82 may be secured to the shaft 14 at a location proximal to the proximal skive hole 22. During the taper forming process, the proximal clamp 82 will remain stationary, while the distal clamp 80 is moved in a distal direction by an automated puller 90 such as an air cylinder mechanism. The automated puller mechanism pulls the shaft during formation a specified distance at a specified rate of travel, which adds uniformity and reliability to the process.

Clamping the catheter shaft in proximal and distal clamps 82 and 80 may serve to arrange the forming area 68 directly in the path of the hot air nozzle fixture, as shown in FIG. 6A or the hot air nozzle fixture may be positioned in the correct location after clamping, depending on the system setup. After correct positioning of the hot air nozzle 72 over the forming area 68, the hot air flow 70 is initiated to heat the forming area 68 for a specified period of time in order to elevate the forming region to temperature at which the polymer material of the shaft 14 will be plastically deformable.

Next, the distal clamp 80 is moved in a distal direction 92 by automated puller 90, as is shown in FIG. 6B. After the pulling stroke is completed, the hot air flow may be discontinued and a brief cooling period with a stream of ambient air (room temperature) initiated onto the forming area 68. After cooling to set the new shape, the shaft is released from the clamps 80 and 82. The insulative material may be cut from the shaft and the tip length trimmed to exact specifications and the cut area radiused to provide a smooth distal terminus.

By way of example, when the above-described inventive process is carried out on a Teflon three lumen papillatome 12 (cross sectional illustration shown in FIG. 9B) of approximate diameter of 0.079 inch+/−0.003 inch after a prior hot die necking operation to reducing the shaft diameter form 0.096 inch, the following process parameters have been shown to be effective. The hot air flow is maintained at 700° F. at a flow rate of 20-30 cfm for a period of 40 seconds. Then pulling is commenced and heat flow is continued during pulling. The pulling distance is on the order of approximately 0.72 inch at a rate of travel of approximately within the range of 0.17 to 0.41 inch/second and preferably 0.29 inch/second.

Preferably, the thermally insulative segments 88 are also configured to provide a radially compressive force to the shaft 14 at their protective locations in addition to providing thermal insulation. Tubular shaped insulative segments that provide some amount of radial compressive force to the shaft are believed to help maintain the shaft material in a consistent form throughout the adjacently applied heating process. The polymer material of the shaft is held in its tubular form and is prevented from flowing under the stress of the heat, which could lead to cracking thin spots that may lead to weakening of the completed shaft assembly. By way of example, as applied to a Teflon papillatome triple lumen shaft of 0.079 inch in diameter+/−0.003, polyolefin shrink tubing of ⅛ inch ID, 0.020 inch recovered nominal wall and approximately ¼ inch in length have been found to be effective as thermal insulators that provide some degree of radial compression to the areas of the shaft adjacent to the forming area 68. Though the shrink tubing initially has an ID of 0.125 inch, which easily slides over the 0.079 inch shaft, after application of heat it shrinks to an inside diameter that is smaller than 0.079 inch, thereby providing a radially compressive force to the shaft.

FIGS. 9A and 9B show cross sectional illustrations of two and three lumen polymer shafts found to be compatible with the process outlined above. The dimensions shown are for shaft material prior to undergoing the preliminary hot die necking operation described above and coincide with a 0.096 outside diameter shaft. As mentioned, above after the necking operation the outside diameter of the shaft is reduced to 0.079 inch. After necking the dimensions shown in the tables below for FIGS. 9A and 9B may be altered accordingly.

In FIG. 9A a two-lumen shaft is shown with a guidewire lumen 16 and cutting wire lumen 18. Several dimensions of the two lumen shaft 100 are identified by reference numeral and presented with corresponding exemplary dimensional values in the table below.

| Reference Numeral | Dimension (in.) |
| --- | --- |
| 102 | .010 |
| 104 | .010 |
| 106 | .010 |
| 108 | .026 |
| 110 | .040 |
| 112 | .096 |

FIG. 9B shows a cross-sectional view of a three lumen shaft 101 having a guidewire lumen 16, cutting wire lumen 18 and a contrast injection lumen 19. The dimensions of a triple lumen polymer shaft are formed from Teflon, having been found to be compatible with the above-described process, is presented in the table below with reference to FIG. 9B.

| Reference Numeral | Dimension (in.) |
| --- | --- |
| 114 | .008 (min) |
| 116 | .008 (min) |
| 118 | .007 (min) |
| 122 | .040 (+.000/−.002) |
| 124 | .028 (+.000/−.002) |
| 126 | .008 (min) |
| 128 | .008 (min) |
| 130 | .097 (+.002/−.001) |

Several elements of the above-described process are especially noteworthy in achieving the low profile short tapered distal tip of the present invention. First, the presence of the thermally insulative segments 88 limits the area of heat application to only the forming area 68 that is desired to be deformed into a tapered shape. This prevents adjacent areas from becoming heated and being stretched when pulling is commenced. Rather, the stretching of the shaft material occurs over only a defined area, promoting a tape that is of pronounced diameter reduction over the relatively short length. Additionally, when the thermally insulative segments are configured to provide radially compressive support to the shaft, unwanted flowing or weakening of the shaft material adjacent to the forming area 68 is prevented. This is especially important in weakened areas such as the location of the distal skive hole 24, which with material already removed, would be more susceptible to cracking, weakening or failure from the heating and stretching operation.

Another improvement of the current system is the step of grasping the shaft both proximally and distally of the forming area 68 by mechanical clamps 80 and 82 and pulling of the distal clamp in the distal direction to stretch the forming area. This arrangement of clamping and pulling serves to better maintain the forming area 68 in the area of the heat source. In the prior art method shown in FIGS. 5A and 5B, in which the shaft is clamped only distally of the forming area and then pulled manually at a proximal location on the shaft, in a proximal direction, it can be seen (in FIG. 5B) that the forming area is pulled slightly away from the direct hot air flow 70'. This movement of the intended forming area 68 away from the heat source causes a greater area of the shaft 14 to be exposed to heat and thus become stretched during the pulling operation. These areas of the shaft adjacent to the forming area are especially susceptible to the heat without the thermally insulative segments in place. That heating of unintended adjacent areas of the shaft tends to draw the taper out over a longer area of shaft during pulling. This occurrence reduces the ability to keep the tip length short while achieving a lower profile or diameter over a shorter taper length.

Maintaining the amount of and thus the strength of the material in the distal tip are provides an additional benefit of permitting two lumens to be open to the distal terminus 42 of the catheter. Therefore a dedicated distally facing contrast injection port 47 (FIG. 2) open to contrast injection lumen 19 can be provided to facilitate contrast injection to the treatment region during use. Without sufficient material left in the tip in the effort to reduce diameter, only one lumen open at the distal terminus might be safely provided without cracking of the tip material. Such an arrangement might require that the injection lumen 19 be merged with the guidewire lumen 16 at a more proximal location to share a distally facing access port through the distal face of the catheter. However by forcing contrast injection through the lumen and distal port already occupied by the guide wire reduces injection capability and performance.

Accordingly, an improved catheter distal tip having a low profile and a short and tapered tip has been demonstrated as well as processes for its manufacture.

It should be understood however, that the foregoing description of the invention is intended merely to be illustrative thereof and that other modifications, embodiments and equivalents may be apparent to those who are skilled in the art without departing from its spirit.

Having thus described the invention what I desire to claim and secure by Letters Patent is:

1. A catheter comprising:
   a shaft comprising proximal and distal ends;
   a tip at the distal end of the shaft having a tapered portion over which the tip outer diameter is gradually reduced;
   a distal terminus;
   an untapered length of shaft positioned adjacent the tapered portion opposite the distal terminus;
   two or more lumens, at least one of which is sized to receive a 0.035 inch guidewire, the lumens spaced apart from one another such that a periphery of one lumen is spaced apart from a periphery of another lumen by a predetermined distance in the untapered length, a corresponding distance between the periphery of said one lumen and the periphery of said another lumen in the tapered portion being different from the predetermined distance in the untapered portion; and
   a cutting wire extending through at least a portion of one of the lumens and terminating within the tip,
   wherein the distal terminus has an outer diameter measuring less than approximately 0.063 inch; and
   wherein the tapered portion of the tip has a length of approximately 3 millimeters or less.

2. A catheter as defined in claim 1 wherein the cutting wire exits the lumen along a portion of the shaft and reenters the lumen through a distal skive hole in the untapered length of the shaft;
   a length between the distal skive hole and the distal terminus is approximately 5 millimeters or less; and
   the tapered portion is positioned between the skive hole and the distal terminus.

3. A catheter as defined in claim 1, further comprising a radiopaque marker within the tip.

4. A catheter as defined in claim 3, wherein the radiopaque marker is contained in the lumen occupied by the cutting wire.

5. A catheter as defined in claim 1 wherein the shaft comprises three lumens.

6. A catheter as defined in claim 1 wherein at least two lumens extend to and open to the distal terminus of the catheter.

7. A catheter as defined in claim 1 wherein the distal terminus has an outer diameter in the range of approximately 0.055 inch to 0.063 inch.

8. A catheter as defined in claim 1 wherein the distal terminus has an outer diameter of approximately 0.059 inch or less.

9. A catheter as defined in claim 1, wherein the cutting wire exits the lumen along a portion of the shaft and reenters the lumen through a distal skive hole in the untapered length of the shaft;
   a length between the distal skive hole and the distal terminus is within the range of 4.5 to 6 mm; and
   the tapered portion is positioned between the skive hole and the distal terminus.

10. A catheter as defined in claim 1, wherein the distance between the lumens in the tapered portion is less than the predetermined distance.

11. A catheter comprising:
    a shaft comprising proximal and distal ends;
    a tip at the distal end of the shaft having a tapered portion over which the tip outer diameter is gradually reduced;
    a distal terminus;
    an untapered length of shaft adjacent the tapered portion opposite the distal terminus;
    two or more lumens, at least one of which is sized to receive a 0.035 inch guidewire, the lumens being spaced apart from one another such that a periphery of one lumen is spaced apart from a periphery of another lumen by a predetermined distance in the untapered length, a corresponding distance between the periphery of said one lumen and the periphery of said another lumen in the tapered portion being different from the predetermined distance; and
    a cutting wire extending through at least a portion of one of the lumens and terminating within the tip,
    wherein the distal terminus has an outer diameter within the range of 0.055 inch to 0.063 inch; and
    wherein the tapered portion of the tip has a length within the range of 1.5 mm to 4.5 mm.

12. A catheter according to claim 11, wherein the outer diameter of the distal terminus is approximately 0.059 inch.

13. A catheter according to claim 11, wherein the length of the tapered portion of the tip is approximately 3 mm.

14. A catheter as defined in claim 11, wherein the shaft comprises three lumens.

15. A catheter as defined in claim 11, wherein at least two lumens extend to and open to the distal terminus of the catheter.

16. A catheter as defined in claim 11, wherein the distance between the lumens in the tapered portion is less than the predetermined distance.

* * * * *